United States Patent
De Lazzari et al.

(10) Patent No.: US 9,808,427 B2
(45) Date of Patent: Nov. 7, 2017

(54) SWALLOWABLE N-ACETYLCYSTEINE TABLETS

(71) Applicant: ZAMBON S.P.A., Bresso, MI (US)

(72) Inventors: Alessandra De Lazzari, Padua (IT); Alberto Moretto, Ponte San Niccolo' (IT)

(73) Assignee: ZAMBON S.P.A., Bresso (Milan) (IT)

(*) Notice: Subject to any disclaimer, the term of this patent is extended or adjusted under 35 U.S.C. 154(b) by 0 days.

(21) Appl. No.: 14/893,100

(22) PCT Filed: May 27, 2014

(86) PCT No.: PCT/EP2014/060950
§ 371 (c)(1),
(2) Date: Nov. 23, 2015

(87) PCT Pub. No.: WO2014/191410
PCT Pub. Date: Dec. 4, 2014

(65) Prior Publication Data
US 2016/0113876 A1   Apr. 28, 2016

(30) Foreign Application Priority Data

May 29, 2013   (IT) .............................. MI2013A0874

(51) Int. Cl.
*A61K 9/20*    (2006.01)
*A61K 31/198*  (2006.01)
*A61K 9/16*    (2006.01)

(52) U.S. Cl.
CPC .......... *A61K 9/2054* (2013.01); *A61K 9/2009* (2013.01); *A61K 9/2027* (2013.01); *A61K 9/2095* (2013.01); *A61K 31/198* (2013.01); *A61K 9/1688* (2013.01)

(58) Field of Classification Search
CPC .................................................. A61K 9/2095
See application file for complete search history.

(56) References Cited

U.S. PATENT DOCUMENTS

| 5,401,514 A | 3/1995 | Juch et al. |
| 2003/0003148 A1* | 1/2003 | Guo ..................... A61K 9/2054 424/468 |

FOREIGN PATENT DOCUMENTS

| EP | 1165065 A1 | 1/2002 |
| EP | 2574333 A1 | 4/2013 |
| WO | 0059500 A1 | 10/2000 |
| WO | 2011128230 A1 | 10/2011 |

OTHER PUBLICATIONS

Jambhekar ("Bioavailability and Granule Properties" Chapter 19 in Handbook of Pharmaceutical Granulation Technology, 2005, Taylor and Francis, pp. 535-543 provided).*
Finholt et al. (Norsk Farm Selsk 1966; 28:238-252).*
Dekhuijzen et al. (International J. of COPD, 2006:1(2), p. 99-106).*
International Search Report of PCT/EP2014/060950 dated Jul. 8, 2014.
De Caro, et al., "Pharmacokinetics and bioavailability of oral acetylcysteine in healthy volunteers," Arzneim.-Forsch/Drug Res. 39(I) Nr. 3 (1989) pp. 382-386.

* cited by examiner

*Primary Examiner* — Robert Havlin
(74) *Attorney, Agent, or Firm* — Silvia Salvadori, P.C.; Silvia Salvadori

(57) ABSTRACT

This invention relates to swallowable tablets containing at least 80% by weight of N-acetylcysteine (NAC) and at least one pharmaceutically acceptable excipient, in particular tablets in which the sulfurous odor is absent, characterized in that the said tablets are assembled using a granulate prepared by means of a process of dry granulating the active ingredient alone, with which the excipients are mixed before compression.

11 Claims, 1 Drawing Sheet

SWALLOWABLE N-ACETYLCYSTEINE TABLETS

This application is a U.S. national stage of PCT/EP2014/060950 filed on 27 May 2014, which claims priority to and the benefit of Italian Application No. MI2013A000874 filed on 29 May 2013, the contents of which are incorporated herein by reference in their entireties.

This invention relates to swallowable tablets having a high content of N-acetylcysteine (NAC), in particular tablets from which the sulfurous odor is absent.

It is known that NAC is a substance having a mucolytic action, which reduces the viscosity of mucus, breaking the disulfide bridges in glycoproteins.

NAC is usually administered topically or orally, in the form of aerosol, syrups, granules or tablets.

NAC is an acid molecule characterized by an unpleasant taste and a sulfurous smell, a smell which becomes stronger during the stages of producing drugs containing NAC and during storage within primary containers.

After oral administration, in man NAC is quickly and completely absorbed in the gastrointestinal tract (De Caro, L., Ghizzi, A., Costa, R., et al. Pharmacokinetics and bioavailability of oral acetylcysteine in healthy volunteers. Arzneim. Forsch. 1989; 39: 382-385).

The particular tropism of this molecule for the pulmonary tissue and for bronchial secretions makes it possible to achieve pharmacologically active concentrations approximately 3 hours after taking the drug. Elimination of NAC and its metabolites takes place essentially via the kidneys.

NAC can be used in the course of chronic diseases of the respiratory tract, which represent the $3^{rd}$ most common cause of death in Italy and the primary cause of invalidity in the European Community. Chronic obstructive pulmonary disease (COPD) is the main cause; this is defined as a preventable and treatable lung disease characterized by persistent bronchial obstruction of the airflow, often associated with significant extrapulmonary symptoms, which can contribute to the severity of clinical manifestations in individual patients.

20% of the Italian population over the age of 65 has COPD, but it is also a non-negligible problem in youth, in that it has been found from epidemiological studies that 10% of young persons between 20 and 44 have coughs and expectoration without ever having developed bronchial obstruction, while 3.6% present symptoms of advanced stage bronchial obstruction.

Regardless of any logical prediction, the overall prevalence of COPD will increase enormously when the consequences of the habit of smoking tobacco (the main risk factor for development of the disease) become apparent in developing countries, and costs, which are already high, will increase in proportion to ageing of the population, increased prevalence and the cost of existing medical treatments and public health.

COPD is a complex disease, with many components involved in its genesis, including mucosal hypersecretion, oxidative stress and inflammation of the airways and lungs.

Smoke and other risk factors (occupational exposure to dusts, gases and smoke, environmental pollution and, particularly in developing countries, domestic pollution) give rise to an inflammatory response which is both bronchopulmonary and systemic, and is capable of maintaining itself even once the irritating agent has been removed, for example after ceasing the habit of smoking. Recent studies appear to indicate that in COPD inflammation is not confined to the lungs but can also be found systemically, thus giving rise to extrapulmonary clinical signs which include muscular weakness, cardiovascular system disease, osteoporosis, hypertension, depression, deterioration of cognitive functions, sleep disturbances, sexual dysfunctions and diabetes.

Oxidative stress seems to play an important part in the pathogenesis of the disease; in smokers and patients with COPD there is an imbalance between oxidizing agents and antioxidants in favor of the former. A central characteristic of the pathogenesis of COPD is also the reduced production of glutathione (GSH, Reduced-Glutathione), an important antioxidant, in the alveoli and lungs, brought about by cigarette smoke.

In patients affected by COPD there is also hyperproduction of mucus by the caliciform cells and the submucosal glands, the accumulation of which in the airways gives rise to numerous functional consequences: diminution of mucociliary clearance, obstruction of the airways and a predisposition to recurrent respiratory infections.

COPD is in fact frequently characterized by episodes in which the symptoms again become acute, during which there is an amplification of the inflammatory and oxidative processes, which often result in hospitalization, especially in patients with the more severe disease, with a consequent dramatic increase in mortality (at 2 years it is 49%, similar to that of lung cancer), worsening in the quality of life and increased direct and indirect costs.

Mucoactive agents are capable of altering the physical and chemical properties of bronchial secretions, aiding their expectoration or reducing their production. In individuals suffering from COPD a number of mucolytic and mucoregulatory agents used over a long period have also been shown to be capable of significantly reducing the number of repeated acute episodes.

The mucoactive, antinflammatory and antioxidant properties of NAC make this drug suitable for the treatment of chronic bronchitis (CB) and COPD, particularly in individuals having a moderate-severe grade of the disease with frequent acute episodes requiring hospitalization.

It has in fact been shown that when administered in a dose of 1200 mg per day (2 tablets of 600 mg each), NAC is effective and safe in the long-term treatment of COPD.

High-dose NAC is also used as an antidote in paracetamol intoxication and to control uropathy brought about by chemotherapy treatments with iso- and cyclophosphamide.

DETAILED DESCRIPTION OF THE INVENTION

Most pack inserts for commercially available drugs containing NAC mention that the possible presence of a sulfurous odor does not mean that there has been any deterioration in the preparation, but that it is a specific property of the active ingredient contained in them.

In the past this unpleasant effect has discouraged the preparation of solid swallowable oral forms containing NAC in high doses, such as for example 600 mg tablets, because of the need to mask the unpleasant sulfurous odor caused by the presence of small traces of a degradation product which has the odor of sulfur using substantial quantities of excipients.

The quantity of excipients which has to be used for this purpose is generally so high as to make the tablets quite large, thus making it difficult and unpleasant to swallow them.

High-dose NAC is normally in fact formulated in an effervescent and non-swallowable form; in this way the high content of excipients (including flavorings) can provide better masking of the sulfurous odor released by the tablet.

In any event, the effervescent tablets are dissolved in water, with the result that the patient perceives the very acidic and unpleasant taste of NAC.

In an attempt to overcome these disadvantages the Applicant has described the preparation of tablets containing high-dose NAC characterized by a reduced sulfurous odor, of a size such that they can be readily swallowed and avoiding the unpleasant taste of NAC remaining in the oral cavity, in European Patent EP 1165065. In these tablets NAC is granulated with a binder solution, by means of a wet process, which includes a heating stage to eliminate the water added to the mass. The granulate so obtained can then be mixed with suitable functional excipients and converted into tablets.

In order to contain the bad odor as far as possible and to limit its release the said tablets are subsequently coated with a film to create a barrier against diffusion of the sulfurous odor from inside the tablet. The tablets described in EP 1165065 contain 80% to 95% by weight of NAC with respect to the total weight of the tablet, and from 0.5% to 4% by weight of a binding agent with respect to the weight of NAC, and being of small size can be readily swallowed.

Despite the effort made by the Applicant the problem has not been resolved in a completely satisfactory manner, because the unpleasant odor can still be perceived by patients before the tablet is administered, at the time when the blister is opened, because of slow diffusion of the sulfurous odor across the coating film during storage.

Unexpectedly the present inventors have found that by modifying the procedure for preparing swallowable tablets containing high-dose NAC in a simple but extremely effective way it is possible to obtain tablets in which the sulfurous odor is no longer present.

This result is even more surprising given that it has been achieved without having to resort to the addition of masking and flavoring agents known in pharmaceutical art in order to improve the olfactory perception.

The changes made to the production process mean that firstly it is no longer necessary to use complex combinations of different pharmaceutically acceptable excipients and that a stage in the production process which is expensive in terms of money and time, such as wet granulation, can be changed into a simpler and more economical stage such as dry granulation.

In fact as a result of this major change it is possible to eliminate the stage of external film coating of the tablets, which is a further process stage that is expensive in terms of money and time, without however compromising ease of swallowing.

The present inventors have achieved this brilliant result through the preparation of a granulate obtained without the addition of binding aqueous solutions, comprising only NAC, which has to be mixed with the remainder of the formulation before compression. This granulate is obtained by the dry compacting of NAC in a single step, thus avoiding the active ingredient from coming into contact with water and with the heat necessary to remove it.

The NAC granulate so obtained has good compressibility characteristics and is suitable for producing tablets with a high content of active ingredient of, for example, between 80% and 95% by weight. By then mixing this granulate with pharmaceutically acceptable excipients, preferably with a suitable binding agent, and compressing the mixture, it is possible to obtain tablets, advantageously without a film-forming stage, which are virtually odorless even after prolonged storage time in a blister. Avoiding film forming in fact makes it possible to eliminate another stage in the process in which degradative stresses such as high temperature and humidity are present.

A first object of this invention therefore relates to a swallowable tablet containing at least 80% by weight of NAC and pharmaceutically acceptable excipients characterized in that the said tablet is assembled using a granulate prepared by means of a dry process for granulating the active ingredient alone.

This process makes it possible to obtain swallowable tablets with a high dose of NAC.

Preferably the tablets according to the invention comprise at least one pharmaceutically acceptable excipient selected from the group comprising binding agents, diluents, disintegrating agents, lubricating agents and glidants.

Advantageously the tablets according to the invention comprise at least one binder in a quantity of 5% or more by weight with respect to the total weight of the tablet.

Advantageously the tablets according to the invention comprise at least one diluent in a quantity of 5% or more by weight with respect to the total weight of the tablet.

Advantageously the tablets according to the invention comprise at least one disintegrating agent in a quantity of 5% or more by weight with respect to the total weight of the tablet.

Advantageously the tablets according to the invention comprise at least one lubricant in a quantity of 1% or less by weight with respect to the total weight of the tablet.

Advantageously the tablets according to the invention comprise at least one glidant in a quantity of 1% or less by weight with respect to the total weight of the tablet.

Advantageously the tablets formulated and produced according to the invention are quickly disintegrating and dissolving tablets with suitable physical properties.

Surprisingly the tablets formulated and produced according to the invention do not give rise to a sulfurous odor even after a prolonged storage time.

In addition to this, the tablets formulated and produced according to the invention bring about a saving in production times and costs, because the process of production for preparing the tablets according to EP 1165065 requires several steps which include drying of the granulate and the stage of film forming in attempt to mask the sulfurous odor.

By the term "swallowable tablet" is meant a tablet for oral administration which is to be swallowed as such or subdivided into two parts, but is not first dissolved in water.

Preferably the tablets formulated and produced according to the invention comprise 80% to 95% by weight of NAC, more preferably from 80% to 90% by weight of NAC with respect to the total weight of the tablet.

Pharmaceutically acceptable excipients which may be included in the tablets according to this invention comprise:
  binders such as for example: hydroxypropyl cellulose (HPC), hydroxypropylmethyl cellulose (HPMC), polyethylene glycol (PEG), methyl cellulose (MC), povidone (PVP), modified starches and others;
  diluents such as for example: microcrystalline cellulose (MCC), anhydrous lactose or lactose monohydrate, pregelatinized starch, mannitol, isomaltose, sorbitol and similar carbohydrates, anhydrous dicalcium phosphate or dicalcium phosphate dihydrate, maltodextrin and others;
  disintegrating agents such as for example: crospovidone, sodium croscarmellose, sodium starch glycolate, partly pregelatinized starch and others;

lubricants such as for example: Ca stearate, Mg stearate, sodium stearyl fumarate, stearic acid and others; and glidants such as for example: anhydrous colloidal silica, talc and others.

In a preferred aspect the tablets according to this invention for example comprise as binding agents: hydroxypropyl cellulose, hydroxypropylmethyl cellulose or polyethylene glycol; as diluents microcrystalline cellulose, mannitol, isomaltose or sorbitol; as disintegrating agents crospovidone, sodium croscarmellose; as lubricants Ca stearate, Mg stearate or sodium stearyl fumarate; and as glidants anhydrous colloidal silica or talc.

In an even more preferred aspect the tablets according to this invention comprise: as binding agent hydroxypropyl cellulose; as diluent microcrystalline cellulose; as disintegrating agent crospovidone; as lubricant Mg stearate and as glidant colloidal silica.

Advantageously, the tablets according to the invention comprise at least one binder in a quantity of between 5% and 10% by weight with respect to the total weight of the tablet.

Advantageously, the tablets according to the invention comprise at least one diluent in a quantity of between 5% and 10% by weight with respect to the total weight of the tablet.

Advantageously, the tablets according to the invention comprise at least one disintegrating agent in a quantity of between 5% and 10% by weight with respect to the total weight of the tablet.

Advantageously, the tablets according to the invention comprise at least one lubricant in a quantity of between 0.2% and 1% by weight with respect to the total weight of the tablet.

Advantageously, the tablets according to the invention comprise at least one glidant in a quantity of between 0.2% and 1% by weight with respect to the total weight of the tablet.

As mentioned above, the tablets according to this invention are prepared by a process of dried granulation of NAC alone by compaction of the powder. The resulting granulate is then mixed with the other excipients and compressed.

In a preferred aspect the tablets according to the invention contain a dose of NAC of between 400 mg and 600 mg, more preferably they contain 600 mg of NAC.

According to this invention the tablets containing 600 mg of NAC have an overall weight which varies between 700 mg and 800 mg and preferably between 725 mg and 775 mg.

Preferably, the tablets according to this invention contain a quantity of binder of between 25 mg and 40 mg, and/or a quantity of diluent of between 40 mg and 70 mg, and/or a quantity of disintegrating agent of between 25 mg and 40 mg, and/or a quantity of lubricating agent of between 5 mg and 10 mg, and/or a quantity of glidant of between 2 mg and 5 mg.

The tablets according to this invention have physical characteristics which satisfy the requirements imposed by official Pharmacopoeias. For example the hardness of the tablets is between 7.5 and 12.5 KP, and/or their friability is between 0.10-0.70%, and/or their disintegration time is less than 4 minutes.

In addition to this the tablets claimed in this document have in vitro dissolution characteristics which are comparable to those of the tablets described in patent EP 1165065.

As a demonstration of the above Table 1 shows the percentage of NAC dissolving after 10 minutes when the in vitro dissolution test is performed on a tablet prepared according to the teaching of this patent application (New Formulation) and a tablet prepared according to the teaching of patent EP 1165065 (EP'065 Formulation) within the physiological pH range (pH 1.2-4.5-6.8).

It will be seen that both types of tablets provide a percentage of dissolved active ingredient of 85% or more by weight of the declared content within 15 minutes at all pH values in the physiological range, which is what is required if the dissolution profiles of the two types of immediate release tablets are to be regarded as being similar according to the reference EMA regulatory guideline (CPMP/EWP/QWP/1401/98 Rev. 1: Guideline on the investigation of Bioequivalence).

TABLE 1

| pH | % NAC dissolved New Formulation | % NAC dissolved EP'065 Formulation |
|---|---|---|
| 1.2 | 92 | 92 |
| 4.5 | 90 | 94 |
| 6.8 | 85 | 90 |

It is clear from the above that the advantages of this invention relate firstly to elimination of the sulfurous odor of the high-dose NAC soluble tablets already described in patent EP 1165065 and secondly to improving the production process, which is simpler, faster and cheaper, without any difference in the dissolution and physical characteristics of the tablet as demonstrated in Table 1.

The tablets according to this invention are particularly suitable for administration to patients suffering from CB and COPD.

In particular the tablets according to this invention are particularly appreciated by patients of the female sex, who are more sensitive to the unpleasant sulfurous odor.

A further object of this invention is use of a granulate prepared according to a procedure for the dry granulation of NAC in the preparation of an odor-free swallowable tablet containing at least 80% by weight of NAC and at least one pharmaceutically acceptable excipient.

The following non-restrictive examples and the following figures are provided in order to better illustrate this invention.

EXAMPLE 1

Preparation of Granulate

Figure 1:
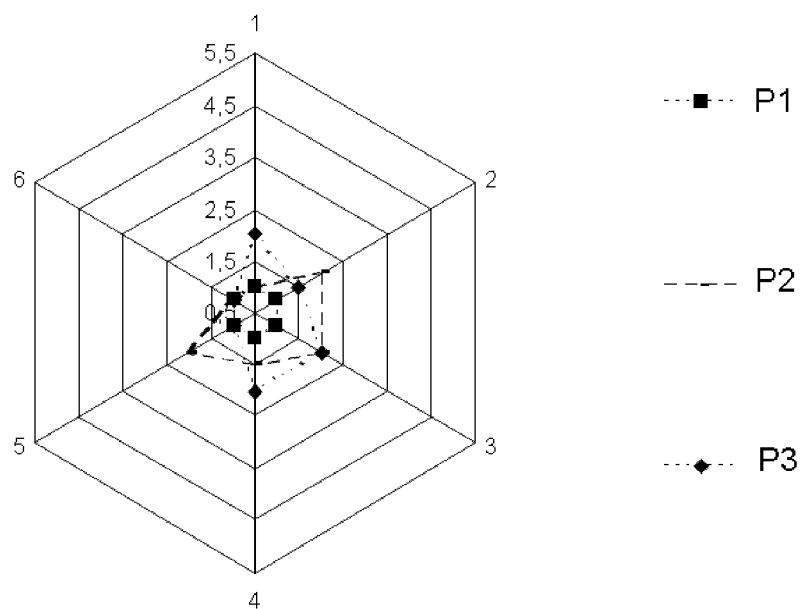
FIG. 1 graphically illustrates the results obtained in olfactory test 2 with the tablet according to the invention.

NAC was dry granulated using a roller compactor. Within this machine two separate stages in the process take place, the powder first passes through two contrarotating rollers which, applying a force to the powder, convert it into a wafer and subsequently the wafer passes through a small mill provided with sieves from which the calibrated granulate emerges.

EXAMPLE 2

Preparation of the Tablets

The granulate produced according to Example 1 was mixed with hydroxypropyl cellulose, microcrystalline cellulose, crospovidone and colloidal silica for 9 minutes and subsequently with Mg stearate for another minute. The mixture produced was compressed using a rotary tablet press applying a compression force of 20 KN and precompression of approximately 3 KN.

The resulting tablets had a hardness of 7.0 KP, a disintegration time of 2 minutes and a friability of 0.2% by weight.

Tablets each having the composition indicated in Table 2 were prepared following the teaching in Examples 1 and 2.

TABLE 2

| Components | Quantity (mg) | % (by weight) |
|---|---|---|
| NAC | 600.0 | 80.00 |
| Crospovidone | 37.5 | 5.00 |
| Microcrystalline cellulose | 63.5 | 8.47 |
| Hydroxypropyl cellulose | 37.5 | 5.00 |
| Anhydrous colloidal silica | 4.0 | 0.53 |
| Mg stearate | 7.5 | 1.00 |
| Total | 750.0 | 100.00 |

EXAMPLE 3

Olfactory Test 1

In order to check whether sulfurous odor was present when opening the pack containing 6 tablets prepared using the dry granulation procedure of the active ingredient according to the invention having the composition shown in Table 2, a test was performed in which 30 individuals were suitably selected in such a way as to rule out smokers, allergic individuals, asthmatics and pregnant women.

The selected individuals were requested:
1. to be free of any colds or any pathological conditions which might compromise their olfactory faculties;
2. not to chew gum or eat at least 30 minutes before the start of the test;
3. not to eat spicy foods during meals consumed before the tests;
4. not to wear perfume, eau de cologne or in any event aftershave or odorous essences on the day of the test;
5. to use perfume-free deodorant on the day of the test;
6. to avoid the use of perfumed cosmetics and personal hygiene products on the day of the test;
7. to have clean and odor-free hands on the day of the test;
8. to have odor- or perfume-free clothing on the day of the test;
9. not to influence the other individuals by comments on the samples tested.

Given these preliminary requirements the individuals selected were each placed in an odorless space (olfactory laboratory) devoid of visible and auditory sensory stimuli, in order to allow each one to concentrate on their specific task.

Before entering the olfactory laboratory the individuals were asked to remain in a comfortable and relaxing environment to reduce environmental stress to a minimum, and they were provided with only water to drink.

Once transferred to the olfactory laboratory each individual was separately asked to open a blister containing 6×600 mg tablets of NAC prepared in accordance with Examples 1 and 2 of this invention and to report the olfactory perception detected at the time of opening and when swallowing the tablet selected from the 6 available.

None of the individuals undergoing the test stated that they perceived a sulfurous odor on opening the pack, nor of having been aware of any odor at the time when they swallowed the tablet.

EXAMPLE 4

Olfactory Test 2

A test was performed with 6 suitably selected individuals trained to evaluate the best olfactory performance offered by the tablets prepared using the processes in Examples 1 and 2 and having the composition shown in Table 2 above (hereinafter the tablets according to the invention) in comparison with the tablets prepared according to Example 19 in patent EP 1165065 (hereinafter the comparison tablets).

The olfactory test was performed in accordance with the protocol described below, using tablets stored for at least one year at 25° C. and 60% relative humidity in the final pack, which comprised an aluminum blister.

These individuals, selected to exclude smokers, allergic individuals, asthmatics and pregnant women, were requested:
1. to be free of any colds or any pathological conditions which might compromise their olfactory faculties;
2. not to chew gum or eat at least 30 minutes before the start of the test;
3. not to eat spicy foods during meals consumed before the tests;
4. not to wear perfume, eau de cologne or in any event aftershave or odorous essences on the day of the test;
5. to use perfume-free deodorant on the day of the test;
6. to avoid the use of perfumed cosmetics and personal hygiene products on the day of the test;
7. to have clean and odor-free hands on the day of the test;
8. to have odor- or perfume-free clothing on the day of the test;
9. not to influence the other individuals by comments on the samples tested.

Given these preliminary requirements the individuals selected were each placed in an odorless space (olfactory laboratory) devoid of visible and auditory sensory stimuli, in order to allow each one to concentrate on their specific task.

Before entering the olfactory laboratory the individuals were asked to remain in a comfortable and relaxing environment to reduce environmental stress to a minimum, and they were provided with only water to drink.

The selected individuals were taken into the olfactory laboratory one at a time and each was then asked to open a blister containing 6 tablets according to the invention and then a blister containing 6 comparison tablets and to describe the olfactory perception experienced according to the method described below:

P1: instantaneous perception of the sulfurous odor at the time when the blister was opened, holding the blister approximately 50 cm from the face (to simulate the normal procedure by which patients open blisters);
P2: perception of the sulfurous odor from the open blister containing the tablet approximately 5 cm from the nose;
P3: perception of the sulfurous odor holding the tablet in the hand at a distance of approximately 5 cm from the nose.

The results were expressed using the following assessment scale:
5=very strong unpleasant odor;
4=clearly perceptible unpleasant odor;

3=quite perceptible unpleasant odor;
2=just perceptible slightly unpleasant odor;
1=imperceptible odor and no unpleasant perception.

Figure 2:
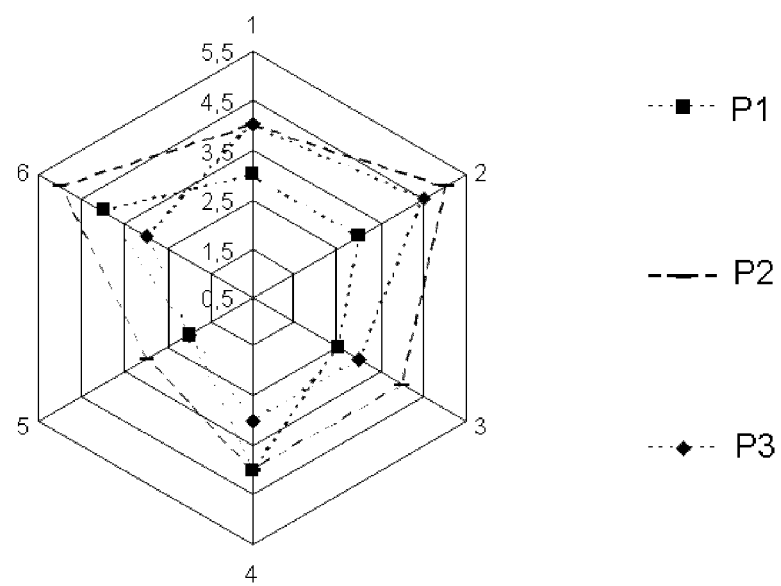
FIG. 2 graphically illustrates the results obtained in olfactory test 2 with the comparison tablet.

The results obtained in the olfactory comparison test have been summarized in Tables 3 and 4 below. FIGS. 1 and 2 graphically illustrate the results in Tables 3 and 4.

TABLE 3

Tablets according to the invention

| Individual | P1 | P2 | P3 |
|---|---|---|---|
| 1 | 1 | 1 | 2 |
| 2 | 1 | 2 | 1.5 |
| 3 | 1 | 2 | 2 |
| 4 | 1 | 1.5 | 2 |
| 5 | 1 | 2 | 1 |
| 6 | 1 | 1 | 1 |

TABLE 4

Comparison tablets

| Individual | P1 | P2 | P3 |
|---|---|---|---|
| 1 | 3 | 4 | 4 |
| 2 | 3 | 5 | 4.5 |
| 3 | 2.5 | 4 | 3 |
| 4 | 4 | 4 | 3 |
| 5 | 2 | 3 | 2 |
| 6 | 4 | 5 | 3 |

The results obtained showed that perception of the sulfurous odor released by the tablets according to the invention was appreciably less than the perception acquired from the comparison tablets, even after a prolonged period of storage in the original blister.

The invention claimed is:

1. A swallowable tablet consisting of at least 80% by weight of N-acetylcysteine, at least one binder in a quantity of 5% or more, at least one disintegrating agent in a quantity of 5% or more, at least one diluent in a quantity of 5% or more, at least one lubricant in quantity of 1% or less, and at least one glidant in a quantity of 1% or less, wherein all percentages are expressed by weight with respect to the total weight of the tablet, wherein said tablet is manufactured using a granulate prepared by a process of the dry granulation of N-acetylcysteine alone.

2. The tablet as claimed in claim 1, in which said binder is selected from the group consisting of hydroxypropyl cellulose (HPC), hydroxypropylmethyl cellulose (HPMC), polyethylene glycol (PEG), methyl cellulose (MC), povidone (PVP) and modified starches.

3. The tablet as claimed in claim 1, in which said disintegrating agent is selected from the group consisting of crospovidone, sodium croscarmellose, sodium starch glycolate and partly pregelatinized starch.

4. The tablet as claimed in claim 1, in which said lubricating agent is selected from the group consisting of Ca stearate, Mg stearate, sodium stearyl fumarate and stearic acid.

5. The tablet as claimed in claim 1, in which said glidant is selected from the group consisting of anhydrous colloidal silica and talc.

6. The tablet as claimed in claim 1, said tablet comprising at least one binder selected from the group comprising hydroxypropyl cellulose, hydroxypropylmethyl cellulose or polyethylene glycol; at least one diluent selected from the group comprising microcrystalline cellulose, mannitol, isomaltose or sorbitol; at least one disintegrating agent selected from the group comprising crospovidone or sodium croscarmellose; at least one lubricant selected from the group comprising Ca stearate, Mg stearate or sodium stearyl fumarate and at least one glidant selected from the group comprising anhydrous colloidal silica or talc.

7. The tablet as claimed in claim 1, wherein said tablet comprises a quantity of N-acetylcysteine between 400 mg and 600 mg.

8. The tablet as claimed in claim 7, wherein said tablet comprises a quantity of 600 mg of N-acetylcysteine.

9. A method of treating patients suffering from CB and/or COPD, said method comprising:
    administering an effective amount of the tablet of claim 1 to said patients; and
    treating said CB and/or COPD.

10. The method as claimed in claim 9, wherein the patients are of the female sex.

11. A process for the preparation of a swallowable tablet according to claim 1, said process comprising (a) a granulation stage, in which an N-acetylcysteine granulate is obtained by the dry granulation of N-acetylcysteine alone, (b) a mixing stage in which the N-acetylcysteine granulate obtained in stage (a) is mixed with at least one binder, diluent, disintegrating agent, lubricant or glidant, and (c) a compression stage in which the mixture obtained in stage (b) is compressed in a the said tablet compressor.

* * * * *